(12) United States Patent
Drysdale et al.

(10) Patent No.: US 7,812,173 B2
(45) Date of Patent: Oct. 12, 2010

(54) TETRAHYDRO-1,8-DIOXA-4A-AZA-NAPHTHALENES IN COATING APPLICATIONS

(75) Inventors: Neville Everton Drysdale, Newark, DE (US); Laura Ann Lewin, Greenville, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 967 days.

(21) Appl. No.: 11/506,004

(22) Filed: Aug. 17, 2006

(65) Prior Publication Data

US 2007/0060771 A1    Mar. 15, 2007

Related U.S. Application Data

(60) Provisional application No. 60/710,476, filed on Aug. 23, 2005, provisional application No. 60/710,377, filed on Aug. 23, 2005.

(51) Int. Cl.
*D21H 21/16* (2006.01)

(52) U.S. Cl. ............ 548/175; 548/218; 423/335; 562/49

(58) Field of Classification Search ............ 562/49
See application file for complete search history.

(56) References Cited

U.S. PATENT DOCUMENTS

| 4,501,679 | A  |   | 2/1985  | Reierson et al. |
| 6,124,479 | A  | * | 9/2000  | Hinoue et al. ............ 549/334 |
| 7,135,530 | B2 |   | 11/2006 | Drysdale et al. |
| 7,148,316 | B2 |   | 12/2006 | Drysdale et al. |
| 7,230,112 | B2 |   | 6/2007  | Adelman et al. |
| 7,355,050 | B2 |   | 4/2008  | Drysdale et al. |
| 7,439,354 | B2 |   | 10/2008 | Lenges et al. |
| 7,504,440 | B2 |   | 3/2009  | Drysdale et al. |
| 7,504,459 | B2 |   | 3/2009  | Drysdale et al. |
| 2005/0074615 | A1 |   | 4/2005 | Adelman et al. |
| 2006/0069025 | A1 |   | 3/2006 | Drysdale et al. |
| 2006/0128873 | A1 |   | 6/2006 | Drysdale et al. |
| 2007/0049752 | A1 |   | 3/2007 | Drysdale et al. |

FOREIGN PATENT DOCUMENTS

| DE | 32 35 933 A1    | 3/1984  |
| FI | 82445           | 11/1990 |
| WO | WO 92/13907     | 8/1992  |
| WO | WO 96/08308     | 3/1996  |
| WO | WO 97/31073     | 8/1997  |
| WO | WO 2005/058912 A1 | 6/2005 |

OTHER PUBLICATIONS

Goldschmidt et al., Tetrahedron Letters, 1994, 35(39), 7272-7276.*
Averse et al. J. Heterocyclic Chem., 1989, 26, 1383.*
PCT International Search Report and Written Opinion for International Application No. PCT/US2006/032729 dated Apr. 11, 2007.

* cited by examiner

*Primary Examiner*—Melvin C Mayes
*Assistant Examiner*—Yun Qian
(74) *Attorney, Agent, or Firm*—Brian J Myers

(57) ABSTRACT

The present disclosure relates to the preparation and use of tetrahydro-1,8-dioxa-4a-aza-naphthalenes in low VOC coatings.

7 Claims, No Drawings

TETRAHYDRO-1,8-DIOXA-4A-AZA-NAPHTHALENES IN COATING APPLICATIONS

CROSS-REFERENCE APPLICATIONS

This application claims the priority benefit of U.S. Provisional Application 60/710,476, filed on Aug. 23, 2005; and Provisional Application, 60/710,377, filed on Aug. 23, 2005.

FIELD OF THE INVENTION

The disclosure herein relates to the preparation and use of tetrahydro-1,8-dioxa-4a-aza-naphthalenes in low VOC coatings.

BACKGROUND OF THE INVENTION

There is a need for film-forming materials that can be part of low VOC (volatile organic compounds) cross-linked systems for coating and other applications. Such materials generally react and cross-link through non-volatile ring-opening additions with poly(isocyanates) to form these coatings, which exhibit desirable final product properties.

One class of these materials is tetrahydro-1,8-dioxa-4a-aza-naphthalenes. These compounds are novel, and the synthetic methods are novel as well.

Additionally, the hydrolyzed tetrahydro-1,8-dioxa-4a-aza-naphthalenes are novel, as are low VOC coatings made by crosslinking these hydrolyzed materials with isocyanates. Generally, by "low VOC" is meant less than about 2.1 pounds of applicable organic solvent(s) is contained in a gallon of paint, as determined under the procedure provided in ASTM D3960.

SUMMARY OF THE INVENTION

Disclosed herein is a composition having the structure:

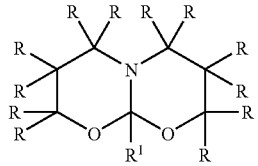

wherein each R and $R^1$ is independently H, C1-C20 alkyl, C6-C20 aromatic, alkylaromatic or aromatic/alkyl. R and $R^1$ optionally can be independently substituted with hydroxyl, amine, epoxy, or carboxy groups.

The disclosure herein further relates to a process to produce tetrahydro-1,8-dioxa-4a-aza-naphthalene of the structure

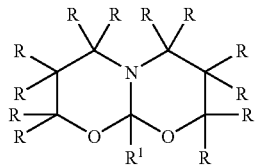

wherein each R and $R^1$ is independently H, C1-C20 alkyl, C6-C20 aromatic, alkylaromatic or aromatic/alkyl, said process comprising:

reacting a 3-(3-hydroxypropylamino)-propan-1-ol with one or more orthoesters of the formula $(R^2O)_3C-R^1$, in the presence of an acid catalyst, optionally in the presence of a solvent;
collecting any alcohol; and
neutralizing by addition of an amine to form a tetrahydro-1,8-dioxa-4a-aza-naphthalene.

The disclosure herein further relates to a composition, comprising: one or more tetrahydro-1,8-dioxa-4a-aza-naphthalenes of the structure

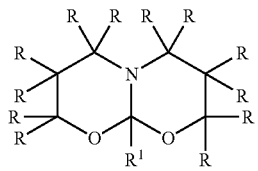

wherein each R and $R^1$ can be independently C1-C20alkyl, C6-C20 aromatic, C6-C20 alkylaromatic or C6-C20 aromati-calkyl; and a crosslinking moiety.

It further relates to the process of making a coating comprising the tetrahydro-1,8-dioxa-4a-aza-naphthalenes and a crosslinking moiety, and coating systems comprising such coatings.

DETAILED DESCRIPTION

There is a need for materials that can be part of low VOC (volatile organic compounds) cross-linked systems for coating and other applications. Such materials generally react and cross-link with poly(isocyanates) to form these coatings, which exhibit desirable final product properties.

One class of these materials is tetrahydro-1,8-dioxa-4a-aza-naphthalenes. These compounds are novel, and the synthetic methods are novel as well.

A new, efficient synthetic route for the production of tetrahydro-1,8-dioxa-4a-aza-naphtalenes, shown generally in structure 1 below, has been discovered.

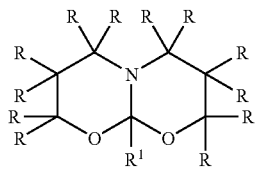

The process for producing tetrahydro-1,8-dioxa-4a-aza-naphthalenes described herein involves the reaction of 3-(3-hydroxypropylamino)-propan-1-ols with orthoesters at elevated temperature. 3-(3-hydroxypropylamino)-propan-1-ols are readily prepared via the procedure described in Finnish Patent No. 82445, assigned to Neste Oy, Finland, incorporated herein by reference. By "elevated temperature" is meant equal to or greater than the boiling point of methanol (65° C.). This reaction is performed optionally in the presence of a solvent, and in the presence of an acid catalyst (for example, toluenesulfonic acid, docecylbenzenesulfonic acid), with the concurrent removal of the liberated alcohol as depicted in Reaction Scheme 1. After the theoretical amount of alcohol is removed, the reaction is cooled and then a small amount of amine is added to neutralize the acid. The final product may then be isolated.

Reaction Scheme 1

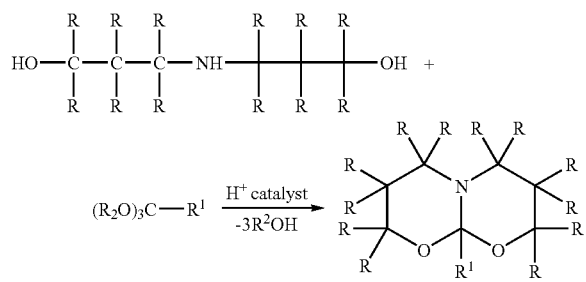

Therefore, the desired end-products are made very easily, with relatively high yields.

In the structures and schemes above, each of R and $R^1$ independently represent H, C1-C20 alkyl, C6-C20 aromatic, alkylaromatic or aromatic/alkyl.

Many orthoesters can be used in the present disclosure. Non-limiting examples of such orthoesters include trimethyl orthoacetate, triethyl orthoacetate and ortho-n-valeric acid trimethyl ester.

Solvents can optionally be used as shown herein. Such solvents are generally non reactive. Non-limiting examples of such solvents include toluene and xylene.

Amines that can be used in the present disclosure include C1-C20 trialkylamines and pyridine. Triethylamine is generally preferred.

The tetrahydro-1,8-dioxa-4a-aza-naphthalenes thus formed by the process of the present disclosure find use in formulating low volatile organic compound (VOC) coatings. These coatings are useful in the automotive and architectural markets.

Examples of isolation methods include distillation and crystallization. As shown in the Examples below, fractional vacuum distillations afford the desired material as a liquid, generally water-clear.

The present disclosure also relates to the discovery that tetrahydro-1,8-dioxa-4a-aza-naphthalenes of general structure, 1, can be used with crosslinking moieties, including multifunctional isocyanates, to gives low VOC coating compositions.

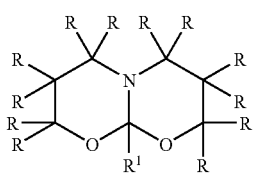

1

The crosslinking (curing) of polymers is an important commercial activity, useful, for example, in elastomers, in coatings, and in thermoset materials such as are used for electronics. Controlling when and under what conditions crosslinking takes place is usually critical since once a polymer is crosslinked it is usually not "workable," that is it may not be reshaped. In some applications, such as coatings and electronic applications it may be desirable or even mandatory that no lower molecular weight compounds be volatilized during or after the crosslinking of the polymers, so as not to contaminate sensitive equipment such as electronics, and/or to pollute the environment, as in the case of coatings.

Numerous ways have been found to avoid the production of volatile compounds during curing. For example, the ring-opening reaction of epoxy groups with other groups such as hydroxyl groups may accomplish this result, but it is sometimes difficult to control after the ingredients are mixed. Furthermore, higher temperatures may be required for this operation. To avoid these types of problems, especially in coatings which often must be cured under conditions close to ambient conditions and which often must be stable for long periods before curing, other solutions have been found, such as the use of spiroorthoesters, see for example patent application PCT 97/31073. However new and/or improved methods of crosslinking polymers are needed.

For coatings, basecoat-clearcoat systems have found wide acceptance in the past decade as automotive finishes. Continuing effort has been directed to such coating systems to improve the overall appearance, the clarity of the topcoat, and the resistance to deterioration. Further effort has been directed to the development of coating compositions having low volatile organic content (VOC). A continuing need exists for coating formulations which provide outstanding performance characteristics after application.

In repairing damage, such as dents to auto bodies, the original coating in and around the damaged area is typically sanded or ground out by mechanical means. Some times the original coating is stripped off from a portion or off the entire auto body to expose the bare metal underneath. After repairing the damage, the repaired surface is coated, preferably with low VOC coating compositions, typically in portable or permanent low cost painting enclosures, vented to atmosphere to remove the organic solvents from the freshly applied paint coatings in an environmentally safe manner. Typically, the drying and curing of the freshly applied paint takes place within these enclosures. Furthermore, the foregoing drying and curing steps take place within the enclosure to also prevent the wet paint from collecting dirt or other contaminants in the air.

As these paint enclosures take up significant floor space of typical small auto body paint repair shops, these shops prefer to dry and cure these paints as fast as possible. More expensive enclosures are frequently provided with heat sources, such as conventional heat lamps located inside the enclosure to cure the freshly applied paint at accelerated rates. Therefore, to provide more cost effective utilization of shop floor space and to minimize fire hazards resulting from wet coatings from solvent based coating compositions, there exists a continuing need for low VOC fast curing coating formulations which cure under ambient conditions while still providing outstanding performance characteristics.

By polymers herein are meant those entities with number average molecular weight from about 100 to about 100,000. Preferably, the number average molecular weight of the polymers is from about 100 to about 10000.

By oligomers herein is meant those polymers which have a number average molecular weight less than about 3000.

The tetrahydro-1,8-dioxa-4a-aza-naphthalenes described herein are crosslinkable. The crosslinking reaction can be initiated when water comes in contact with these tetrahydro-1,8-dioxa-4a-aza-naphthalenes to hydrolyze them. By water is meant water in the pure form, moisture, moist air, moist gas or mixture of gases, or any other aqueous or non-aqueous media in which water may be present in a homogeneous or a heterogeneous mixture. Such media may be in the liquid form or the gaseous form.

When the tetrahydro-1,8-dioxa-4a-aza-naphthalene is hydrolyzed, amino hydroxy ester is formed as illustrated below. The amino hydroxy ester and the amide diol exist simultaneously as the reaction of conversion of the amino hydroxy ester to amide diol can be controlled by time, temperature, pH, and the urethane forming catalyst present in the reaction mixture. In the case of the amino hydroxy ester the reactive sites are the secondary amine and the hydroxyl groups.

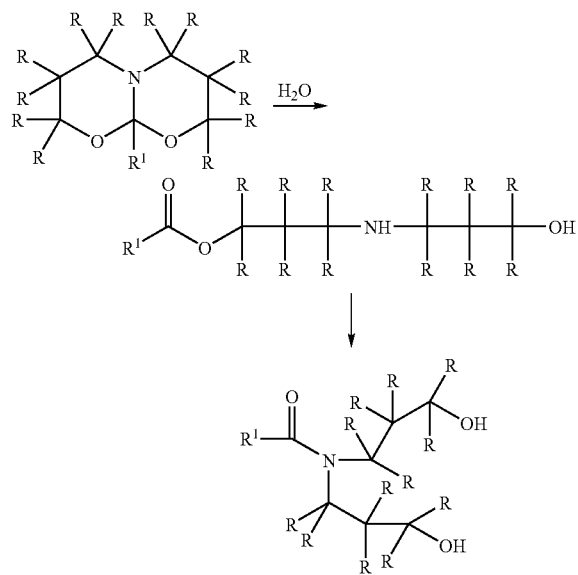

Note that in this reaction, no relatively volatile low molecular weight products are produced, i.e., no harmful volatile by-products are released. Since these reactions may optionally be acid catalyzed some of the ring opening of the tetrahydro-1,8-dioxa-4a-aza-naphthalene may lead to cationic polymerization rather than simple ring opening. Herein preferably the major molar portion of the tetrahydro-1,8-dioxa-4a-aza-naphthalene present may simply ring open and polymerize, preferably at least about 75 mole percent, and more preferably at least 90 molar percent may simply ring open and polymerize. The polymerization occurs generally at high temperatures. It is of course recognized that, although only one tetrahydro-1,8-dioxa-4a-aza-naphthalene group is shown.

In the compositions, and in the materials used in the processes herein, the tetrahydro-1,8-dioxa-4a-aza-naphthalene groups may be included by a variety of methods. In one instance, the tetrahydro-1,8-dioxa-4a-aza-naphthalene may be included as a "monomeric" compound, which may hydrolyze, thus providing reactive hydroxyl groups.

Alternatively, the tetrahydro-1,8-dioxa-4a-aza-naphthalene groups may be part of a polymer. For example a dihydroxy tetrahydro-1,8-dioxa-4a-aza-naphthalene (which has not yet been hydrolyzed) may be reacted with an excess of a diisocyanate such as bis(4-isocyanatophenyl)methane (MDI), toluene diisocyanate (TDI), hexamethylene diisocyanate (HMDI) or isophorone diisocyanate (IPDI) to form an isocyanate-ended polymer. In turn, exposure of the isocyanate-ended polymer to water results in hydrolysis of the tetrahydro-1,8-dioxa-4a-aza-naphthalene to form hydroxyl groups. These hydroxyl groups react with the remaining isocyanate groups.

Other diols such as ethylene glycol or 1,4-butanediol may also be copolymerized into the isocyanate-ended polymer. It is noted that in this type of isocyanate-ended polymer, the tetrahydro-1,8-dioxa-4a-aza-naphthalene group is (at least before hydrolysis) part of the main chain (not on a branch).

Alternately, the tetrahydro-1,8-dioxa-4a-aza-naphthalene may be functionalized, for example, via reaction of (mono) hydroxy tetrahydro-1,8-dioxa-4a-aza-naphthalene with isocyanate to give urethane tetrahydro-1,8-dioxa-4a-aza-naphthalene, or with diisocyanates, for example, 1,6-hexamethylene diisocyanate, to give diurethane ditetrahydro-1,8-dioxa-4a-aza-naphthalenes, or DESMODUR® 3300 commercially available from Bayer Corporation, Pittsburgh, Pa. which contains multifunctional isocyanates, such as triisocyanate, to give the corresponding multifunctional urethane tetrahydro-1,8-dioxa-4a-aza-naphthalenes. Many of these compounds are novel.

Examples of suitable polyisocyanates include aromatic, aliphatic or cycloaliphatic di-, tri- or tetra-isocyanates, including polyisocyanates having isocyanurate structural units, such as, the isocyanurate of hexamethylene diisocyanate and isocyanurate of isophorone diisocyanate; the adduct of 2 molecules of a diisocyanate, such as, hexamethylene diisocyanate and a diol such as, ethylene glycol; uretidiones of hexamethylene diisocyanate; uretidiones of isophorone diisocyanate or isophorone diisocyanate; the adduct of trimethylol propane and meta-tetramethylxylylene diisocyanate.

Additional examples of suitable polyisocyanates include 1,2-propylene diisocyanate, trimethylene diisocyanate, tetramethylene diisocyanate, 2,3-butylene diisocyanate, hexamethylene diisocyanate, octamethylene diisocyanate, 2,2,4-trimethyl hexamethylene diisocyanate, 2,4,4-trimethyl hexamethylene diisocyanate, dodecamethylene diisocyanate, omega, omega -dipropyl ether diisocyanate, 1,3-cyclopentane diisocyanate, 1,2-cyclohexane diisocyanate, 1,4-cyclohexane diisocyanate, isophorone diisocyanate, 4-methyl-1,3-diisocyanatocyclohexane, trans-vinylidene diisocyanate, dicyclohexylmethane-4,4'-diisocyanate, 3,3'-dimethyl-dicyclohexylmethane 4,4'-diisocyanate, a toluene diisocyanate, 1,3-bis(1-isocyanato 1-methylethyl)benzene, 1,4-bis(1-isocyanato-1-methylethyl) benzene, 1,3-bis(isocyanatomethyl) benzene, xylene diisocyanate, 1,5-dimethyl-2,4-bis(isocyanatomethyl)benzene, 1,5-dimethyl-2,4-bis (2-isocyanatoethyl)benzene, 1,3,5-triethyl-2,4-bis (isocyanatomethyl)benzene, 4,4'-diisocyanatodiphenyl, 3,3'-dichloro-4,4'-diisocyanatodiphenyl, 3,3'-diphenyl-4,4'-diisocyanatodiphenyl, 3,3'-dimethoxy-4,4'-diisocyanatodiphenyl, 4,4'-diisocyanatodiphenylmethane, 3,3'dimethyl-4,4'-diisocyanatodiphenyl methane, a diisocyanatonaphthalene, polyisocyanates having isocyanaurate structural units, the adduct of 2 molecules of a diisocyanate, such as, hexamethylene diisocyanate or isophorone diisocyanate, and a diol such as ethylene glycol, the adduct of 3 molecules of hexamethylene diisocyanate and 1 molecule of water (available under the trademark Desmodur® N from Bayer Corporation of Pittsburgh, Pa.), the adduct of 1 molecule of trimethylol propane and 3 molecules of toluene diisocyanate (available under the trademark Desmodur® L from Bayer Corporation), the adduct of 1 molecule of trimethylol propane and 3 molecules of isophorone diisocyanate, compounds such as 1,3,5-triisocyanato benzene and 2,4,6-triisocyanatotoluene, and the adduct of 1 molecule of pentaerythritol and 4 molecules of toluene diisocyanate.

In another embodiment, one can form a polymer, preferably an acrylic polymer having isocyanate groups (from, for example, 2-isocyanatoethyl (meth)acrylate). This acrylic polymer can then be reacted with a tetrahydro-1,8-dioxa-4a-aza-naphthalene moiety, wherein one of the R or $R^1$ groups contains a hydroxyl, amine or carboxy group. The acrylic polymer will have at least one tetrahydro-1,8-dioxa-4a-azanaphthalene group, but may and preferably will have more than one. The number of tetrahydro-1,8-dioxa-4a-aza-naphthalene groups present in the acrylic polymer will depend on the reaction stoichiometry and the amount of isocyanate groups present in the acrylic polymer.

In one instance a first polymer containing intact (before hydrolysis) tetrahydro-1,8-dioxa-4a-aza-naphthalene groups, and a crosslinking agent containing functional groups that can react with hydroxyl or secondary amine groups. The crosslinking agent may be a monomeric compound such as a diisocyanate such as MDI, TDI, HMDI or IPDI, or an epoxy resin, or may be a polymer containing crosslinking functional groups. For example it may be (meth)acrylate copolymer containing repeat units derived from 2-isocyanatoethyl (meth)acrylate or glycidyl (meth)acrylate. It is also possible that the first polymer and the crosslinking agent are "combined" in the same polymer. For example, one can copolymerize a tetrahydro-1,8-dioxa4a-aza-naphthalene with 2-isocyanatoethyl (meth)acrylate or glycidyl (meth)acrylate and optionally other copolymerizable monomers. When that single polymer is exposed to moisture, presumably the tetrahydro-1,8-dioxa4a-aza-naphthalene groups will hydrolyze forming amino hydroxy groups, which in turn will react with the isocyanate, carboxylic acid anhydride, melamine, silane(s) or epoxide groups, whichever are present. These materials may be combined as a single polymer or may be more than one substance.

In one embodiment, a second polymer which has functional groups capable of reacting with hydroxyl or secondary amines has a number average molecular weight less than 3000. A preferred functionality for this second polymer is isocyanate.

A specific example of the crosslinking agent, or second polymer with functional groups capable of reacting with hydroxyl or secondary amines, used here is the Desmodur® 3300 compound from Bayer. The idealized structure of Desmodur® 3300 is given as follows (also, pentamer, heptamer and higher molecular weight species can be present):

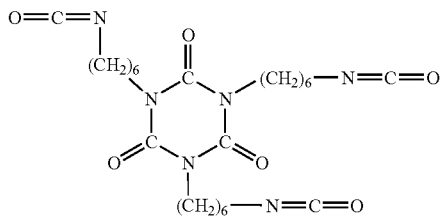

Also present in these compositions, as tetrahydro-1,8-dioxa4a-aza-naphthalenes and the processes in which they are used, is a material having a functional group which reacts with hydroxyl or secondary amine groups. This reaction should take place under the conditions chosen for the crosslinking reaction. Ambient, heating or other conditions may be used to initiate the reaction. Preferably the reaction with hydroxyl or secondary amine groups should not produce any volatile low molecular weight compounds, except those normally found in air ($CO_2$, water, etc.). Typical groups which react with hydroxyl or secondary amine groups include isocyanates (including isocyanurate trimers), epoxides, carboxylic acid anhydrides (especially those which are parts of polymers), melamine, and silane(s). Isocyanates, melamine and silane are especially preferred for coatings. Typically the ratio of equivalents of isocyanate to amine and/or hydroxyl is between 1:1 and 1.8:1.

In any of the compositions herein, the polymeric materials may range from relatively low to relatively high molecular weight. It is preferred that they be of relatively low molecular weight so as to keep the viscosity of the compositions before crosslinking low, so as to avoid or minimize the need for solvent(s).

The compositions herein may contain water. It is to be understood that as the water contacts the tetrahydro-1,8-dioxa-4a-aza-naphthalene groups present in the composition, the tetrahydro-1,8-dioxa-4a-aza-naphthalene groups will start to hydrolyze, eventually leading to crosslinking of the composition. The water may be introduced in a variety of ways. For example, especially in the case of a coating the water may introduced into the uncrosslinked or crosslinking (while the crosslinking is taking place) coating by absorption from the air. This is very convenient for making an uncrosslinked coating composition which is stable until exposed to (moist) air. Alternatively water may be mixed in a mixing head or spray mixing head (for a coating) just before crosslinking is to take place. This is particularly useful for making thicker crosslinked items such as electronic encapsulants where diffusion of moisture into a thicker section will take longer. The introduction of water can be at a point where the final shape of the polymeric crosslinked part can be formed before crosslinking takes place.

Other materials which may optionally be present in the compositions and processes include one or more solvents (and are meant to act only as solvents). These preferably do not contain groups such as hydroxyl or primary or secondary amino that can react with functional groups and/or tetrahydro-1,8-dioxa-4a-aza-naphthalenes. One or more catalysts for the hydrolysis of tetrahydro-1,8-dioxa-4a-aza-naphthalenes may be present. These are typically Brönsted acids, but these acids should not be so strong as cause substantial cationic ring opening polymerization of the tetrahydro-1,8-dioxa-4a-aza-naphthalenes and/or epoxides which may be present. If substantial cationic ring opening polymerization of tetrahydro-1,8-dioxa-4a-aza-naphthalene groups takes place, this can often lead to premature crosslinking of the composition. The same caveats may be said for any catalysts which may be present which catalyze the reaction of hydroxyl groups or the amino hydroxy groups with the first or second functional groups. What these catalysts may be will depend on what the first or second functional group(s) present are. Such catalysts are known in the art.

Some of the suitable catalysts for polyisocyanate can include one or more tin compounds, tertiary amines or a combination thereof; and one or more aforedescribed acid catalyst. Suitable tin compounds include dibutyl tin dilaurate, dibutyl tin diacetate, stannous octoate, and dibutyl tin oxide. Dibutyl tin dilaurate is preferred. Suitable tertiary amines include triethylene diamine. One commercially available catalyst that can be used is Fastcat® 4202 dibutyl tin dilaurate sold by Elf-AtoChem North America, Inc. Philadelphia, Pa. It is acknowledged that one skilled in the art could use acetic acid or such weak acids to block the activity of the catalyst.

The present compositions, and the process for making them crosslinked, are useful as encapsulants, sealants, and coatings. The coating composition of this disclosure can be used as a clear coat that is applied over a pigmented base coat that may a pigmented version of the composition of this disclosure or another type of a pigmented base coat. The clear coating can be in solution or in dispersion form.

Typically, a clear coating is then applied over the base coating before the base coating is fully cured, a so called "wet-on-wet process", and the base coating and clear coating are then fully cured at ambient temperatures or can be cured by heating to elevated temperatures of 40° C to 100° C. for 15 to 45 minutes. The base coating and clear coating preferably have a dry coating thickness ranging from 25 to 75 microns and 25 to 100 microns, respectively.

The novel coating composition may be used as a base coat or as a pigmented monocoat topcoat. Both of these compositions require the presence of pigments. Typically, a pigment-to-binder ratio of 0.1/100 to 200/100 is used depending on the color and type of pigment used. The pigments are formulated into mill bases by conventional procedures, such as, grinding, sand milling, and high speed mixing. Generally, the mill base comprises pigment and a dispersant in an aqueous medium. The mill base is added in an appropriate amount to the coating composition with mixing to form a pigmented coating composition.

Any of the conventionally-used organic and inorganic pigments, such as, white pigments, like, titanium dioxide, color pigments, metallic flakes, such as, aluminum flake, special effects pigments, such as, coated mica flakes, coated aluminum flakes and the like and extender pigments can be used. It may be desirable to add flow control additives.

The novel coating composition may be used as a primer in which case typical pigments used in primers would be added, such as, carbon black, barytes, silica, iron oxide and other pigments that are commonly used in primers in a pigment-to-binder ratio of 150/100 to 300/100.

The coating composition can be applied by conventional techniques, such as, spraying, electrostatic spraying, dipping, brushing, and flow coating.

The coating composition is particularly useful for the repair and refinish of automobile bodies and truck bodies and parts as a clear coat, pigmented base coat, or as a primer. The novel composition has uses for coating any and all items manufactured and painted by automobile sub-suppliers, frame rails, commercial trucks and truck bodies, including but not limited to beverage bodies, utility bodies, ready mix concrete delivery vehicle bodies, waste hauling vehicle bodies, and fire and emergency vehicle bodies, as well as any potential attachments or components to such truck bodies, buses, farm and construction equipment, truck caps and covers, commercial trailers, consumer trailers, recreational vehicles, including but not limited to, motor homes, campers, conversion vans, vans, large commercial aircraft and small pleasure aircraft, pleasure vehicles, such as, snow mobiles, all terrain vehicles, personal watercraft, motorcycles, and boats. The novel composition also can be used as a coating for industrial and commercial new construction and maintenance thereof; cement and wood floors; walls of commercial and residential structures, such as, office buildings and homes; amusement park equipment; concrete surfaces, such as parking lots and drive ways; asphalt and concrete road surface, wood substrates, marine surfaces; outdoor structures, such as bridges, towers; coil coating; railroad cars; printed circuit boards; machinery; OEM tools; signs; fiberglass structures; sporting goods; and sporting equipment.

This makes these coatings particularly useful for repainting of transportation vehicles in the field. An advantage of the present materials and processes in encapsulants and sealants is that when tetrahydro-1,8-dioxa-4a-aza-naphthalenes are used in crosslinking reactions the resulting product does not shrink, or shrink as much as usual in a typical crosslinking reaction. This means any volume to be filled by the crosslinked material will be more reliably filled with a reduced possibility of voids being present due to shrinkage during crosslinking.

For whatever uses they are put to, the compositions, and the materials used in the processes described herein may contain other materials which are conventionally used in such uses. For example, for use as encapsulants and sealants the composition may contain fillers, pigments, and/or antioxidants.

For coatings there may be a myriad of other ingredients present, some of which are described below. In particular there may be other polymers (especially of low molecular weight, "functionalized oligomers") which are either inert or have functional group(s) other than those that may act as the materials comprising tetrahydro-1,8-dioxa4a-aza-naphthalenes and also react with other reactive materials in the coating composition.

Representative of the functionalized oligomers that can be employed as components or potential cross-linking agents of the coatings are the following:

Acid Oligomers: The reaction product of multifunctional alcohols such as pentaerythritol, hexanediol, trimethylol propane, and the like, with cyclic monomeric anhydrides such as hexahydrophthalic anhydride, methylhexahydrophthalic anhydride, and the like.

Hydroxyl Oligomers: The above acid oligomers further reacted with monofunctional epoxies such as butylene oxide, propylene oxide, and the like.

Anhydride Oligomers: The above acid oligomers further reacted with ketene.

Silane Oligomers: The above hydroxyl oligomers further reacted with isocyanato propyltrimethoxy silane.

Epoxy Oligomers: The diglycidyl ester of cyclohexane dicarboxylic acid, such as Araldite® CY—184 from Ciba Geigy, and cycloaliphatic epoxies, such as ERL®—4221, and the like from Union Carbide.

Aldimine Oligomers: The reaction product of isobutyraldehyde with diamines such as isophorone diamine, and the like.

Ketimine Oligomers: The reaction product of methyl isobutyl ketone with diamines such as isophorone diamine.

Melamine Oligomers: Commercially available melamines such as CYMEL® 1168 from Cytec Industries, and the like.

AB-Functionalized Oligomers: Acid/hydroxyl functional oligomers made by further reacting the above acid oligomers with 50%, based on equivalents, of monofunctional epoxy such as butylene oxide or blends of the hydroxyl and acid oligomers mentioned above or any other blend depicted above.

CD-Functionalized Crosslinkers: Epoxy/hydroxyl functional crosslinkers such as the polyglycidyl ether of Sorbitol DCE-358® from Dixie Chemical or blends of the hydroxyl oligomers and epoxy crosslinkers mentioned above or any other blend as depicted above.

The compositions disclosed herein may additionally contain a binder of a noncyclic oligomer, i.e., one that is linear or aromatic. Such noncyclic oligomers can include, for instance, succinic anhydride- or phthalic anhydride-derived moieties in the Acid Oligomers: such as described above.

Preferred functionalized oligomers have weight average molecular weight not exceeding about 3,000 with a polydispersity not exceeding about 1.5; more preferred oligomers have molecular weight not exceeding about 2,500 and polydispersity not exceeding about 1.4; most preferred oligomers have molecular weight not exceeding about 2,200, and polydispersity not exceeding about 1.25. Typically, compositions will comprise from about 20 to about 80 weight percent of the functionalized oligomer based on the total weight of tetrahydro-1,8-dioxa-4a-aza-naphthalene-containing compound in the coating. Preferably compositions will comprise from about 30 to about 70 weight percent of the functionalized oligomer based on the total weight of the tetrahydro-1,8-dioxa-4a-aza-naphthalene-containing compound in the coating. More preferably compositions will comprise from about 40 to about 60 weight percent of the functionalized oligomer based on the total weight of tetrahydro-1,8-dioxa-4a-azanaphthalene-containing compound in the coating. Other additives also include polyaspartic esters, which are the reaction product of diamines, such as, isopherone diamine with dialkyl maleates, such as, diethyl maleate.

The coating compositions may be formulated into high solids coating systems dissolved in at least one solvent. The solvent is usually organic. Preferred solvents include aromatic hydrocarbons such as petroleum naphtha or xylenes; ketones such as methyl amyl ketone, methyl isobutyl ketone, methyl ethyl ketone or acetone; esters such as butyl acetate or hexyl acetate; and glycol ether esters such as propylene glycol monomethyl ether acetate.

The coating compositions are unique in that they retain their flowable nature over time. As described below in the Examples, the novel materials, once combined with the crosslinking moiety, remain water clear and flowable for greater than three months (at least 89 days). While the viscosity of the combined materials increased, they did not gel, and could thus be sprayed.

The coating compositions can also contain a binder of an acrylic polymer of weight average molecular weight greater than 3,000, or a conventional polyester such as SCD®—1040 from Etna Product Inc. for improved appearance, sag resistance, flow and leveling and such. The acrylic polymer can be composed of typical monomers such as acrylates, methacrylates, styrene and the like and functional monomers such as hydroxy ethyl acrylate, glycidyl methacrylate, or gamma methacrylylpropyl trimethoxysilane and the like.

The coating compositions can also contain a binder of a dispersed acrylic component which is a polymer particle dispersed in an organic media, which particle is stabilized by what is known as steric stabilization. Hereafter, the dispersed phase or particle, sheathed by a steric barrier, will be referred to as the "macromolecular polymer" or "core". The stabilizer forming the steric barrier, attached to this core, will be referred to as the "macromonomer chains" or "arms".

The dispersed polymer contains about 10 to 90%, preferably 50 to 80%, by weight, based on the weight of the dispersed polymer, of a high molecular weight core having a weight average molecular weight of about 50,000 to 500,000. The preferred average particle size is 0.1 to 0.5 microns. The arms, attached to the core, make up about 10 to 90%, preferably 10 to 59%, by weight of the dispersed polymer, and have a weight average molecular weight of about 1,000 to 30,000, preferably 1,000 to 10,000. The macromolecular core of the dispersed polymer is comprised of polymerized acrylic monomer(s) optionally copolymerized with ethylenically unsaturated monomer(s). Suitable monomers include styrene, alkyl acrylate or methacrylate, ethylenically unsaturated monocarboxylic acid, and/or silane-containing monomers. Such monomers as methyl methacrylate contribute to a high Tg (glass transition temperature) dispersed polymer, whereas such "softening" monomers as butyl acrylate or 2-ethylhexylacrylate contribute to a low Tg dispersed polymer. Other optional monomers are hydroxyalkyl acrylates or methacrylates or acrylonitrile. Optionally, the macromolecular core can be crosslinked through the use of diacrylates or dimethacrylates such as allyl methacrylate or post reaction of hydroxyl moieties with polyfunctional isocyanates. The macromonomer arms attached to the core can contain polymerized monomers of alkyl methacrylate, alkyl acrylate, each having 1 to 12 carbon atoms in the alkyl group, as well as glycidyl acrylate or glycidyl methacrylate or ethylenically unsaturated monocarboxylic acid for anchoring and/or crosslinking. Typically useful hydroxy-containing monomers are hydroxy alkyl acrylates or methacrylates as described above.

The coating compositions can also contain conventional additives such as pigments, stabilizers, rheology control agents, flow agents, toughening agents and fillers. Such additional additives will, of course, depend on the intended use of the coating composition. Fillers, pigments, and other additives that would adversely effect the clarity of the cured coating will not be included if the composition is intended as a clear coating.

The coating compositions are typically applied to a substrate by conventional techniques such as spraying, electrostatic spraying, roller coating, dipping or brushing. As mentioned above atmospheric moisture may "diffuse" into the coating and cause curing, or alternatively just before the coating is applied it is mixed with an appropriate amount of water, as in a mixing spray head. Under these latter conditions it is important to apply the coating before it crosslinks. The present formulations are particularly useful as a clear coating for outdoor articles, such as automobile and other vehicle body parts. The substrate is generally prepared with a primer and or a color coat or other surface preparation prior to coating with the present compositions.

A layer of a coating composition is cured under ambient conditions in the range of 30 minutes to 24 hours, preferably in the range of 30 minutes to 3 hours to form a coating on the substrate having the desired coating properties. It is understood that the actual curing time depends upon the thickness of the applied layer and on any additional mechanical aids, such as, fans that assist in continuously flowing air over the coated substrate to accelerate the cure rate. If desired, the cure rate may be further accelerated by baking the coated substrate at temperatures generally in the range of from about 60° C. to 150° C. for a period of about 15 to 90 minutes. The foregoing baking step is particularly useful under OEM (Original Equipment Manufacture) conditions.

Unless otherwise stated, all chemicals and reagents were used as received from Aldrich Chemical Co., Milwaukee, Wis.

EXAMPLES

In the Examples below, the following tests and procedures were used:

Film Preparation:

The clearcoats were drawn down over Uniprime (ED-5000, cold-rolled steel (04X12X032)B952 P60 DIW unpolish Ecoat POWERCRON 590 from ACT Laboratories, Hillsdale, Mich.), TPO, using a 6 mil drawdown blade.

Micro-Hardness:

The micro-hardness of the coatings was measured using a Fischerscope hardness tester (model HM100V, Fischer Technologies, Windsor, Conn.). The tester was set for maximum force of 100 mN ramped in series of 50, 1 second steps. The hardness was recorded in $N/mm^2$.

Swell Ratio:

The swell ratio of the free films (removed from TPO) was determined by swelling in methylene chloride. The free film was placed between two layers of aluminum foil and using a LADD punch (Ladd Research, Williston, Vt.), a disc of about 3.5 mm diameter was punched out of the film. The aluminum foil was removed from either side of the free film. Using a microscope with 10× magnification and a filar lens the unswollen diameter ($D_o$) of the film was measured. Four drops of methylene chloride were added to the film, the film was allowed to swell for a few seconds and then a glass slide was placed over it. The swell ratio was then calculated as:

swell ratio=$(D_s)^2/(D_o)^2$

Gel Fraction:

Measured according to the procedure set forth in U.S. Pat. No. 6,221,494 col. 8 line 56 to col. 9 line 2 which procedure is hereby incorporated by reference.

Strike-In:

Strike-in is the interaction between the basecoat and clearcoat, during wet-on-wet application. The degree of interaction is dependent upon the formulation, process parameters and/or ambient conditions. When this interaction is excessive, strike-in, or redissolving, will occur. This will result in a mottled appearance of the basecoat and a "fuzzy" appearance of the clearcoat. Thus, it is critical to minimize this strike-in to maximize appearance. The degree of strike-in can be expressed by measuring the "flop index" or "flop" of a panel. The lower the flop measurement, the greater the strike-in. The flop of samples can be measured on the same day as the basecoat-clearcoat application with a Chromavision MA100, available from DuPont, Wilmington, Del.

Example 1

3,3,6,6,8a-Pentamethyl-tetrahydro-1,8-dioxa-4a-aza-naphthtalene

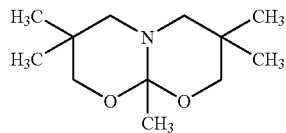

3-(3-Hydroxy-2,2-dimethyl-propylamino)-2,2-dimethyl-propan-1-ol (127.76 g, 0.68 mol), ortho-n-valericacid trimethylester (162.0 g, 1.00 mol) and toluene sulfonic acid (2.0 g) were charged into a oven dried round bottom flask equipped with a stirring bar, distillation head and under nitrogen. The resulting solution was heated until the theoretical amount of ethanol was collected. The reaction was cooled to room temperature and triethylamine added to neutralize the acid. Fractional vacuum distillations (twice) afforded the product as a water clear liquid, boiling point 84.0-86.2° C. at 2.6 torr. Yield: 116 g (53.7%)

Example 2

3,3,6,6,-Tetramethyl-8a-butyl-tetrahydro-1,8-dioxa4a-aza-naphthalene

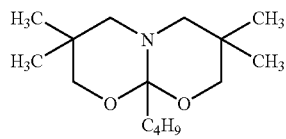

3-(3-Hydroxy-2,2-dimethyl-propylamino)-2,2-dimethyl-propan-1-ol (128.0 g, 0.68 mol), triethyl orthoacetate (162.0 g, 1.00 mol) and toluene sulfonic acid (2.0 g) were charged into a oven dried round bottom flask equipped with a stirring bar, distillation head and under nitrogen. The resulting solution was heated until the theoretical amount of methanol was collected. The reaction was cooled to room temperature and triethylamine added to neutralize the acid. Fractional vacuum distillations (twice) afforded the product as a water clear liquid, boiling point 101-103° C. at 0.44 torr. Yield: 156 g (90.5%).

Example 3

Coating Composition with 3,3,6,6,8a-Pentamethyl-tetrahydro-1,8-dioxa-4a-aza-naphthalene 3,3,6,6,8a-Pentamethyl-tetrahydro-1,8-dioxa-4a-aza-naphthalene (3.20 g, 0.015 mol, as made in Example 1) and Desmodur® 3300 (7.02 g, 0.0138 mol) were placed in a glass vial. To the resulting clear solution was added 0.10 g of a dibutyl tin dilaurate solution (1.58 g dibutyl tin dilaurate in 5 mL propylene glycol monomethyl ether acetate), followed by 0.10 g dodecylbenzenesulfonic acid solution (2.0 g in 3 g of propylene glycol monomethyl ether acetate). The resulting solution was poured on glass plates and allowed to dry overnight, resulting in very hard clear coating. The material remaining in the sealed vial was still flow-able after 2 days.

Example 4

Coating Composition with 3,3,6,6,-Tetramethyl-8a-butyl-tetrahydro-1,8-dioxa-4a-aza-naphthalene 3,3,6,6,-Tetramethyl-8a-butyl-tetrahydro-1,8-dioxa-4a-aza-naphthalene (8.60 g, 0.0337 mol, as made in Example 2) and Desmodur® 3300 (12.97 g, 0.0255 mol) were placed in a glass vial and shaken until a homogeneous solution resulted, then 7.96 g of this solution was withdrawn and placed in a glass vial. To this solution was added 0.10 g of an acetic acid solution (0.317 g in 8.0 g propylene glycol monomethyl ether acetate) followed by dibutyl tin dilaurate (0.03 g) and propylene glycol monomethyl ether acetate (1.0 g). The resulting mixture was shaken until a homogeneous solution resulted and then poured on glass plates and allowed to dry overnight, resulting in clear hard coatings. The solution consisting of 3,3,6,6,-tetramethyl-8a-butyl-tetrahydro-1,8-dioxa-4a-aza-naphthalene and Desmodur® 3300 was still clear and flow-able after 5 days. After about 3 months (at least 89 days) the material remaining in the vial was still water clear and flowable, with somewhat of a viscosity increase.

Example 5

Coating Formulated with 3,3,6,6,8a-Pentamethyl-tetrahydro-1,8-dioxa-4a-aza-naphthalene In a glass jar 8.48 grams of 3,3,6,6,8a-pentamethyl-tetrahydro-1,8-dioxa-4a-aza-napthalenes (as prepared in Example 1) was combined with 2.84 grams of propylene glycol monomethylether acetate, 0.92 grams of a 2% dibutyl tin dilaurate solution in ethyl acetate, and 0.11 grams of a BYK 306 and 0.04 grams of Byk 361. To this was added 68.66 grams of a solution of 32.93 grams of Desmodur® XP 2410 (hexamethylene diisocyaante trimer available from Bayer), 31.38 grams of Desmodur® Z4470BA (isophorone diisocyanate trimer available from Bayer) and 4.35 grams n-butyl acetate. This mixture was stirred and then 0.36 grams of acetic acid was added and the mixture and stirred. The mixture was drawndown to give coatings of ~4 mils in thickness.

The coating was baked at 140° F. for 30 minutes. At one day the coating had a Fischercope hardness of 90 N/mm² and a swell ratio of 1.70. At 30 days the coating had a Fischercope hardness of 158 N/mm², a Tg (at the midpoint) of 59° C. and a gel fraction of 96%.

What is claimed is:

1. A process to produce a tetrahydro-1,8-dioxa-4a-aza-naphthalene of the structure:

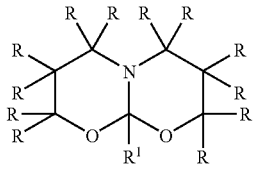

wherein each R and R¹ is independently H, C1-C20 alkyl, C6-C20 aromatic, alkylaromatic or aromatic/alkyl, said process comprising:
reacting a 3-(3-hydroxypropylamino)-propan-1-ol having the structure

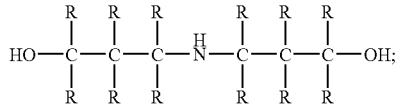

wherein each R is defined as above; with one or more orthoesters of the formula $(R^2O)_3C-R^1$, in the presence of acid catalyst, optionally in the presence of a solvent;
collecting any alcohol; and
neutralizing by addition of an amine to form tetrahydro-1,8-dioxa-4a-aza-naphthalene.

2. The process of claim 1, wherein said orthoester is trimethyl orthoacetate or triethyl orthoacetate.

3. The process of claim 1, wherein said acid catalyst is toluenesulfonic acid.

4. The process of claim 1, wherein said optional solvent is toluene or xylene.

5. The process of claim 1, wherein said amine is a C1-C20 trialkyl amine.

6. The process of claim 1, further comprising isolation of said tetrahydro-1,8-dioxa-4a-aza-naphthalene.

7. The process of claim 6, wherein said isolation is accomplished by distillation, crystallization, or a combination thereof.

* * * * *